United States Patent [19]

Gehring et al.

[11] Patent Number: 4,808,209

[45] Date of Patent: Feb. 28, 1989

[54] 5-FLUOROACYLAMINO-4-NITRO-1-ARYL-PYRAZOLES

[75] Inventors: Reinhold Gehring, Wuppertal; Otto Schallner, Monheim; Jörg Stetter, Wuppertal; Hans-Joachim Santel, Leverkusen; Robert R. Schmidt; Klaus Lürssen, both of Bergisch Gladbach, all of Fed. Rep. of Germany

[73] Assignee: Bayer Aktiengesellschaft, Leverkusen, Fed. Rep. of Germany

[21] Appl. No.: 934,075

[22] Filed: Nov. 24, 1986

[30] Foreign Application Priority Data

Dec. 5, 1985 [DE] Fed. Rep. of Germany ....... 3543035

[51] Int. Cl.⁴ .................. C07D 231/16; C07D 231/40; A01N 43/56
[52] U.S. Cl. ........................................ 71/92; 548/376; 548/362
[58] Field of Search ..................... 548/362, 376; 71/92, 71/; 546/279

[56] References Cited

U.S. PATENT DOCUMENTS 4,589,905 5/1986 Beck .................................... 546/279
4,620,865 11/1986 Beck et al. ......................... 546/279

FOREIGN PATENT DOCUMENTS 3402308 8/1985 Fed. Rep. of Germany ...... 548/362
3520330 12/1986 Fed. Rep. of Germany ...... 546/279
2503706 10/1982 France ................................ 548/362

Primary Examiner—John M. Ford
Attorney, Agent, or Firm—Sprung, Horn, Kramer & Woods

[57] ABSTRACT

Novel 5-fluoroacylamino-4-nitro-1-aryl-pyrazoles of the formula

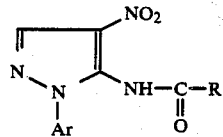

in which
R represents alkyl which is substituted by fluorine and
Ar represents in each case optionally substituted phenyl or pyridyl, exhibit herbicidal and plant growth-regulating activity. The nitro-free corresponding intermediates are also novel.

3 Claims, No Drawings

5-FLUOROACYLAMINO-4-NITRO-1-ARYL-PYRAZOLES

The invention relates to new 5-fluoroacylamino-4-nitro-1-aryl-pyrazoles, several processes for their preparation and their use as herbicides and growth regulators.

It is already known that certain 5-halogenoacylamino-4-nitro-1-aryl-pyrazoles, such as, for example, 5-(ω-chlorobutyramido)-4-nitro-1-(2,6-dichloro-4-trifluoromethylphenyl)-pyrazole, have herbicidal properties (compare DE-OS (German Published Specification) No. 3,402,308) corresponding to U.S. application Ser. No. 690,347, filed Jan. 10, 1984, now allowed.

The herbicidal activity of these already known compounds towards problem weeds is, however, like their tolerance towards important useful plants, not always completely satisfactory in all fields of use.

New 5-fluoroacylamino-4-nitro-1-aryl-pyrazoles of the general formula (I)

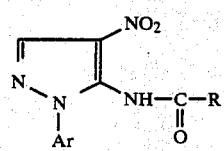

(I)

in which
R represents alkyl which is substituted by fluorine and
Ar represents in each case optionally substituted phenyl or pyridyl,
have been found.

It has furthermore been found that the new 5-fluoroacylamino-4-nitro-1-aryl pyrazoles of the general formula (I)

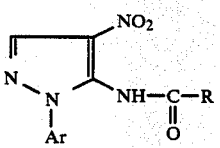

(I)

in which
R represents alkyl which is substituted by fluorine and
Ar represents in each case optionally substituted phenyl or pyridyl,
are obtained by a process in which
(a) 5-amino-4-nitro-1-aryl-pyrazoles of the formula (II)

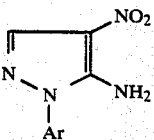

(II)

in which
Ar has the abovementioned meaning,
are reacted with fluoroacyl compounds of the formula (III)

(III)

in which
R has the abovementioned meaning and
E represents an electron-attracting leaving group,
if appropriate in the presence of a diluent and if appropriate in the presence of an acid-binding agent, or by a process in which
(b) 5-fluoroacylamino-1-aryl-pyrazoles which are unsubstituted in the 4-position, of the formula (IV)

(IV)

in which
R has the abovementioned meaning,
are reacted with nitric acid, if appropriate in the presence of a diluent and if appropriate in the presence of a catalyst.

Finally, it has been found that the new 5-fluoroacylamino-4-nitro-1-aryl-pyrazoles of the formula (I) have a herbicidal and growth-regulating action.

Surprisingly, the 5-fluoroacylamino-4-nitro-1-aryl-pyrazoles of the general formula (I) according to the invention have a considerably better herbicidal activity against problem weeds, coupled with a comparably good selectivity for useful plants, than the 5-halogenoacylamino-4-nitro-1-aryl-pyrazoles known from the prior art, such as, for example, 5-(ω-chlorobutyramido)-4-nitro-1-(2,6-dichloro-4-trifluoromethylphenyl)-pyrazole, which are closely related compounds chemically and from the point of view of their action.

Formula (I) provides a general definition of the 5-fluoroacylamino-4-nitro-1-aryl-pyrazoles according to the invention. Preferred compounds of the formula (I) are those
in which
R represents a radical

or represents a radical —A—CF$_3$ and
Ar represents phenyl which is optionally monosubstituted or polysubstituted by identical or different substituents, or represents 2-pyridyl, 3-pyridyl or 4-pyridyl, in each case optionally monosubstituted or polysubstituted by identical or different substituents, possible substituents in each case being: cyano, nitro, halogen, in each case straight-chain or branched alkyl, alkoxy and alkoxycarbonyl with in each case up to 4 carbon atoms, in each case straight-chain or branched halogenoalkyl and halogenoalkoxy with in each case up to 4 carbon atoms and up to 9 identical or different halogen atoms and a radical —S(O)$_m$—R$^3$
wherein R¹ represents hydrogen, fluorine, chlorine or straight-chain or branched halogenoalkyl with 1 to 4 carbon atoms and 1 to 9 identical or different halogen atoms, or represents in each case straight-chain or branched alkyl, alkoxy or alkylthio with in each case 1 to 4 carbon atoms, R² represents hydrogen, fluorine or chlorine, R³ represents amino, or represents in each case straight-chain or branched alkyl, alkylamino, dialkylamino or halogenoalkyl with in each case up to 4 carbon atoms in the individual alkyl parts and, in the case of the halogenoalkyl, with up to 9 identical or different halogen atoms, A represents alkylene which has 1 to 12 carbon atoms and is optionally monosubstituted or polysubstituted by chlorine and m represents the number 0, 1 or 2.

Particularly preferred compounds of the formula (I) are those
in which

R represents a radical

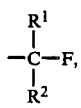

or represents a radical —A—CF₃ and

Ar represents phenyl which is optionally mono-, di-, tri-, tetra- or pentasubstituted by identical or different substituents, or represents 2-pyridyl, 3-pyridyl or 4-pyridyl, in each case optionally mono-, di-, tri- or tetrasubstituted by identical or different substituents, possible substituents in each case being: cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy and a radical —S(O)ₘ—R³, wherein R¹ represents hydrogen, fluorine, chlorine, trifluoromethyl, difluoromethyl, fluoromethyl, dichlorofluoromethyl, difluorochloromethyl, chloromethyl, dichloromethyl, trichloromethyl, pentafluoroethyl, heptafluoropropyl or chlorofluoromethyl, or represents methyl, ethyl, n- or i-propyl, methoxy, ethoxy or methylthio, R² represents hydrogen, fluorine or chlorine, R³ represents amino, methylamino, ethylamino, dimethylamino, diethylamino, fluorodichloromethyl, difluoromethyl, tetrafluoroethyl, trifluorochloroethyl, trifluoromethyl, methyl or ethyl, A represents alkylene which has 1 to 8 carbon atoms and is optionally mono-, di-, tri-, tetra- or pentasubstituted by chlorine and m represents the number 0, 1 or 2.

The following 5-fluoroacylamino-4-nitro-1-arylpyrazoles of the general formula (I) may be mentioned specifically, in addition to the compounds mentioned in the preparation examples:

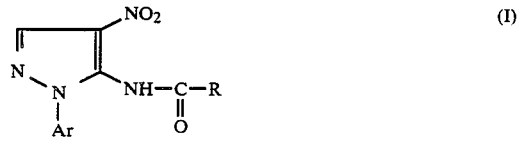

TABLE 1

| R | Ar | R | Ar |
|---|---|---|---|
| —(CF₂)₂—CF₃ | 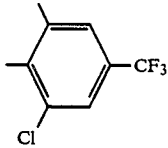 3,5-Cl₂-C₆H₃-CF₃ | —CH₂—CF₃ | 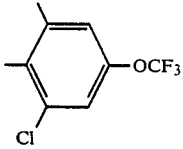 3,5-Cl₂-C₆H₃-OCF₃ |
| —(CF₂)₂—CF₃ | 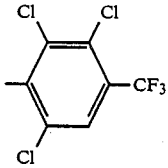 2,4,6-Cl₃-C₆H₂-CF₃ | —CF₂—CHClF | 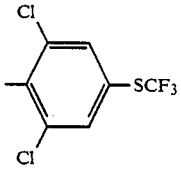 3,5-Cl₂-C₆H₃-SCF₃ |
| —CF₂—CF₃ | 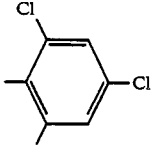 3,4,5-Cl₃-C₆H₂ | —(CF₂)₇—CF₃ | 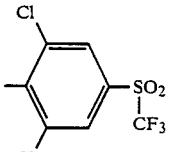 3,5-Cl₂-C₆H₃-SO₂CF₃ |

TABLE 1-continued

| R | Ar | R | Ar |
|---|---|---|---|
| $-(CF_2)_2-CF_3$ | 3-Cl, 6-CF$_3$, 2-methylpyridine | $-CH(Cl)-CH_2-C(Cl)_2-CF_3$ | 2-Cl, 4-CF$_3$ phenyl |
| $-CHF-CH_3$ | 3-Cl, 6-Cl, 2-methylpyridine | $-CF_2-CF_3$ | 2,3,6-triCl, 4-CF$_3$ phenyl |
| $-CF_2-SCH_3$ | 2,6-diCl, 4-CF$_3$ phenyl | $-CF_3$ | 3-Cl, 5-CF$_3$, 2-methylpyridine |
| $-CF(CF_3)-OCH_3$ | 3-Cl, 5-OCF$_3$, 2-methylpyridine | $-CF_3$ | 3-Cl, 5-Cl, 2-methylpyridine |
| $-CF_3$ | 2,5-diCl, 3,6-diF, 4-CF$_3$ phenyl (hexasubstituted) | $-CHF_2$ | 2,5-diCl, 3,6-diF, 4-CF$_3$ phenyl |
| $-CF_3$ | 2,6-diCl, 3,5-diF, 4-CF$_3$ phenyl | $-CHF_2$ | 2,6-diCl, 4-SCF$_3$ phenyl |
| $-CF_3$ | 2,3,4-triCl phenyl | $-CHF_2$ | 2-Cl, 4-OCF$_3$ phenyl |
| $-CF_3$ | 2-Cl, 4-SCF$_3$ phenyl | $-CClF_2$ | 2-Cl, 4-CF$_3$ phenyl |
| $-CF_3$ | 2,6-diCl, 4-SCF$_3$ phenyl | $-CClF_2$ | 2,6-diCl, 3,5-diF, 4-CF$_3$ phenyl |

TABLE 1-continued

| R | Ar | R | Ar |
|---|---|---|---|
| —CF₃ | 3,5-dichloro-4-(OCF₃)phenyl | —CClF₂ | 2,3-dichlorophenyl |
| —CF₃ | 2,3,5-trichloro-4-(OCF₃)phenyl | —CClF₂ | 3-chloro-4-(OCF₃)phenyl |
| —CF₃ | 2,3,5-trichloro-4-(SCF₃)phenyl | —CClF₂ | 3,5-dichloro-4-(SCF₃)phenyl |
| —CHF₂ | 3-chloro-4-(CF₃)phenyl | —CCl₂F | 2,3,5-trichloro-4-(CF₃)phenyl |
| —CHF₂ | 3,5-dichloro-4-(SO₂CF₃)phenyl | —CCl₂F | 3-chloro-4-(CF₃)phenyl |
| —CCl₂F | 3,5-dichloro-4-(SO₂CF₃)phenyl | —CCl₂F | 3,5-dichloro-4-(SCF₃)phenyl |
| —CCl₂F | 3-chloro-4-(OCF₃)phenyl | —CHF₂ | 3-chloro-5-(CF₃)pyridin-2-yl |
| —CHF₂ | 3,5-dichloropyridin-2-yl | —CClF₂ | 3-chloro-5-(CF₃)pyridin-2-yl |
| —CClF₂ | 3,5-dichloropyridin-2-yl | —CCl₂F | 3,5-dichloropyridin-2-yl |

TABLE 1-continued

| R | Ar | R | Ar |
|---|---|---|---|
| —CCl$_2$F | 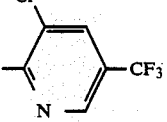 | —CF$_2$CF$_3$ | 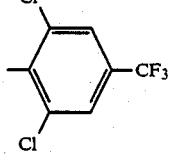 |

If, for example, 5-amino-4-nitro-1-(2,6-dichloro-4-trifluoromethylphenyl)-pyrazole and trifluoroacetic anhydride are used as starting substances, the course of the reaction in process (a) according to the invention can be represented by the following equation:

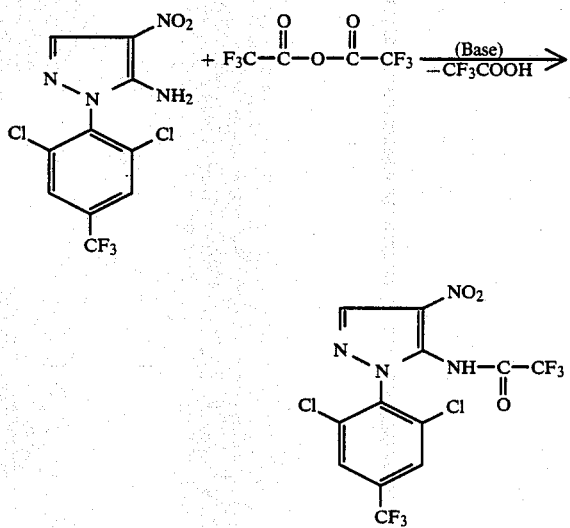

If, for example, 5-trifluoroacetamido-1-(2,3,6-trichloro-4-trifluoromethylphenyl)-pyrazole is used as the starting compound, the course of the reaction in process (b) according to the invention can be represented by the following equation:

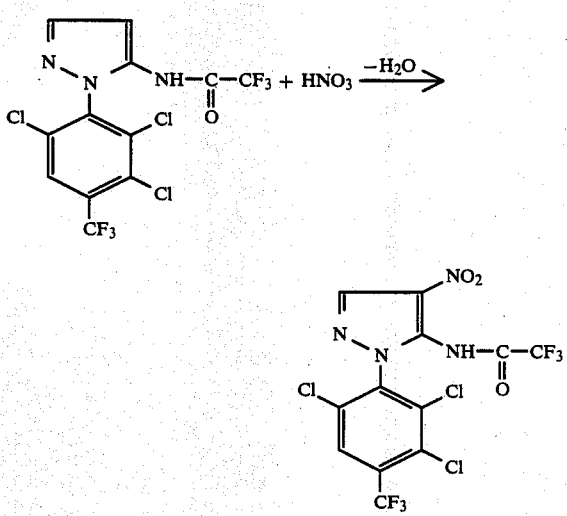

Formula (II) provides a general definition of the 5-amino-4-nitro-pyrazoles required as starting substances for carrying out process (a) according to the invention. In this formula (II), Ar preferably represents those radicals which have already been mentioned as preferred for this substituent in connection with the description of the substances of the formula (I) according to the invention.

The 5-amino-4-nitro-pyrazoles of the formula (II) are known (compare DE-OS (German Published Specification) No. 3,402,308), or they are the subject of commonly assigned German Patent Application DE-P No. 3,520,330 of June 7, 1985, corresponding to U.S. application Ser. No. 866,638, filed May 22, 1986, now pending, and are obtainable by known processes (compare DE-OS (German Published Specification) No. 3,402,308), for example by a procedure in which arylhydrazines of the formula (V)

$$Ar-NH-NH_2 \qquad (V)$$

in which
Ar has the abovementioned meaning, and 2-halogenoacrylonitriles of the formula (VI)

in which
Hal represents halogen, in particular chlorine or bromine,
are either initially reacted in a 1st stage, if appropriate in the presence of a diluent, such as, for example, glacial acetic acid or ethanol, and if appropriate in the presence of a reaction auxiliary, such as, for example, sodium acetate, at temperatures between −20° C. and +20° C., to give the arylhydrazine derivatives of the formula (VII)

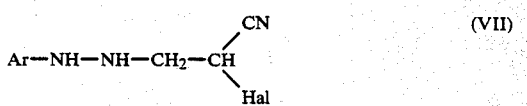

in which
Ar and Hal have the abovementioned meaning,
and these are cyclized in a 2nd stage, if appropriate in the presence of a diluent, such as, for example, ethylene glycol monoethyl ether, and if appropriate in the presence of an acid catalyst, such as, for example, sulphuric acid or phosphoric acid, at temperatures between +50° C. and +150° C., or are cyclized directly in one reaction step, without isolation of the intermediate stage of the formula (VII), if appropriate in the presence of a diluent, such as, for example, ethylene glycol monoethyl ether or ethanol, at temperatures between +50° C. and +150° C., and the 5-aminopyrazoles which are unsubstituted in the 4-position and are thus obtainable, of the formula (VIII)

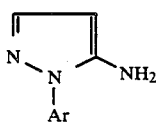

(VIII)

in which
Ar has the abovementioned meaning,
are nitrated in a subsequent reaction with a nitrating agent, such as, for example, nitric acid, if appropriate in the presence of a diluent, such as, for example, glacial acetic acid, and if appropriate in the presence of a reaction auxiliary, such as, for example, acetic anhydride, at temperatures between −20° C. and +50° C.

If appropriate, it may be of advantage for the amino group in the 5-position of the pyrazole ring to be protected with the aid of the customary protective group technique, for example by acylation, before the nitration reaction and for the amino-protective group to be split off again, likewise in the customary manner, for example by hydrolysis with an aqueous or alcoholic base, when the nitration has been carried out.

The arylhydrazines of the formula (V) are known (compare, for example, U.S. Pat. No. 4,127,575; U.S. Pat. No. 3,609,158; DE-OS (German Published Specification) No. 2,558,399; and J. Chem. Soc. C, 1971, 167–174), or they can be obtained by known processes in a simple analogous manner (compare, for example, Houben-Weyl "Methoden der organischen Chemie" ("Methods of organic chemistry") Volume X/2, page 203, Thieme Verlag Stuttgart, 1967), for example by a procedure in which the known anilines or pyridylamines of the formula (IX)

(IX)

in which
Ar has the abovementioned meaning,
are reacted with sodium nitrate in the presence of an acid, such as, for example, sulphuric acid, and then with tin-II chloride, likewise in the presence of an acid, such as, for example, hydrochloric acid, at temperatures between −20° C. and +80° C., or by a procedure in which halogenoaromatics of the formula (X)

(X)

in which
Ar has the abovementioned meaning and
Hal¹ represents halogen, in particular fluorine, chlorine or bromine,
are reacted with hydrazine hydrate, if appropriate in the presence of a diluent, such as, for example, pyridine or dioxane, at temperatures between 0° and 150° C.

The 2-halogenoacrylonitriles of the formula (VI), the anilines and pyridylamines of the formula (IX) and the halogenoaromatics of the formula (X) are generally known compounds of organic chemistry, Formula (III) provides a general definition of the fluoroacyl compounds furthermore required as starting substances for carrying out process (a) according to the invention. In this formula (III), R preferably represents those radicals which have already been mentioned as preferred for this substituent in connection with the description of the substances of the formula (I) according to the invention.

E preferably represents halogen, in particular chlorine or bromine, or represents a radical R—CO—O—, R having the abovementioned meaning.

The fluoroacyl compounds of the formula (III) are generally known compounds of organic chemistry.

Formula (IV) provides a general definition of the 5-fluoroacylamino-1-aryl-pyrazoles which are unsubstituted in the 4-position and are required as starting substances for carrying out process (b) according to the invention. In this formula (IV), R and Ar preferably represent those radicals which have already been mentioned as preferred for these substituents in connection with the description of the substances of the formula (I) according to the invention.

The 5-fluoroacylamino-1-aryl-pyrazoles which are unsubstituted in the 4-position, of the formula (IV), are not yet known. They are obtained, however, by a process analogous to known processes (compare, for example, DE-OS (German Published Specification) No. 3,402,308), by a procedure in which 4-unsubstituted 5-amino-pyrazoles of the formula (VIII)

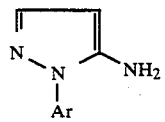

(VIII)

in which
Ar has the abovementioned meaning,
are acylated with fluoroacyl compounds of the formula (III)

(III)

in which
R and E have the abovementioned meaning,
if appropriate in the presence of a diluent, such as, for example, methylene chloride, and if appropriate in the presence of an acid-binding agent, such as, for example, pyridine, analogously to the procedure of process (a) according to the invention at temperatures between −20° C. and +120° C.

Possible diluents for carrying out process (a) according to the invention are inert organic solvents. These include, in particular, aliphatic, alicyclic or aromatic, optionally halogenated hydrocarbons, such as, for example, benzine, toluene, xylene, chlorobenzene, petroleum ether, hexane, cyclohexane, methylene chloride, chloroform or carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric acid triamide, esters, such as ethyl acetate, or sulphoxides, such as dimethylsulphoxide.

If appropriate, process (a) according to the invention is carried out in the presence of a suitable acid-binding agent.

Possible acid-binding agents are all the customary inorganic or organic bases. These include, for example, alkali metal hydroxides, such as sodium hydroxide or potassium hydroxide, alkali metal carbonates, such as sodium carbonate, potassium carbonate or sodium bicarbonate, and tertiary amines, such as triethylamine, N,N-dimethylaniline, pyridine N,N-dimethylaminopyridine, diazabicyclooctane (DABCO), diazabicyclononene (DBN) or diazabicycloundecene (DBU).

The reaction temperatures can be varied within a substantial range in carrying out process (a) according to the invention. The reaction is in general carried out at temperatures between $-20°$ C. and $+150°$ C., preferably at temperatures between $0°$ C. and $+120°$ C.

For carrying out process (a) according to the invention, in general 1.0 to 5.0 mols, preferably 1.0 to 2.0 mols, of fluoroacyl compound of the formula (III) and, if appropriate, 1.0 to 5.0 mols, preferably 1.0 to 2.0 mols, of acid-binding agent are employed per mol of 5-amino-4-nitro-1-aryl-pyrazole of the formula (II). The reaction is carried out and the reaction products of the formula (I) are worked up and isolated by customary, generally known processes.

Possible diluents for carrying out process (b) according to the invention are all the solvents which can usually be employed for such nitration reactions. The acids suitable as reagents, or mixtures thereof, with a catalyst acid, such as, for example, sulphuric acid, nitric acid, acetic anhydride or nitrating acid, are preferably simultaneously used as the diluent. If appropriate, inert organic solvents, such as, for example, glacial acetic acid or chlorinated hydrocarbons, such as methylene chloride, chloroform or carbon tetrachloride, are also suitable as diluents.

Possible catalysts or reaction auxiliaries for carrying out process (b) according to the invention are likewise the catalysts customary for such nitrations; acid catalysts, such as, for example, sulphuric acid or acetic anhydride, are preferably used.

The reaction temperatures can be varied within a substantial range in carrying out process (b) according to the invention. The reaction is in general carried out at temperatures between $-50°$ C. and $+150°$ C., preferably at temperatures between $-20°$ C. and $+120°$ C.

For carrying out process (b) according to the invention, in general 1.0 to 100.0 mols, preferably 1.0 to 50.0 mols, of nitric acid and, if appropriate, 0.1 to 10 mols of catalyst are employed per mol of 5-fluoroacylamino-1-aryl-pyrazole which is unsubstituted in the 4-position, of the formula (IV). The reaction is carried out and the reaction products of the formula (I) are worked up and isolated by customary, generally known processes.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can thereby be used with particularly good success for selectively combating monocotyledon and dicotyledon weeds, in particular in monocotyledon crops, such as barley or wheat.

The precursors of the formula (IV) also exhibit a good herbicidal activity when applied in appropriate amounts.

The active compounds according to the invention moreover engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide.

As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example lignin-sulphite waste liquors and methyl cellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

When used as herbicides, the active compounds according to the invention, as such or in the form of their formulations, can also be used, for combating weeds, as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N′-dimethyl-urea, for combating weeds in cereals; 4-aminno-3-methyl-6-phenyl-1,2,4-triazin-5(4H)-one, for combating weeds in sugar beet, and 4-amino-6-(1,1-dimethylethyl)-3-methylthio-1,2,4-triazin-5(4H)-one for combating weeds in soya bean. Mixtures with N,N-dimethyl-N′-(3-chloro-4-methylphenyl)-urea; N,N-dimethyl-N′-(4-isopropylphenyl)-urea; 4-amino-6-t-butyl-3-ethylthio-1,2,4-triazin-5(4H)-one; 2,4-dichlorophenoxyacetic acid; 2,4-dichlorophenoxypropionic acid; (2-methyl-4-chlorophenoxy)-acetic acid; (4-chloro-2-methylphenoxy)-propionic acid; 2-benzyloxyethyl, trimethylsilylmethyl or 2,2-diethoxyethyl 2-[4-(3,5-dichloropyrid-2-yloxy)-phenoxy]-propionate; methyl 5-(2,4-dichlorophenoxy)-2-nitrobenzoate; 3,5-diiodo-4-hydroxybenzonitrile; 3-isopropyl-2,1,3-benzothiadiazin-4-one 2,2-dioxide; 2-chloro-N-{[(4-methoxy-6-methyl-1,3,5-triazin-2-yl)-amino]-carbonyl}-benzenesulphonamide; 4-ethylamino-2-t-butylamino-6-methylthio-s-triazine; N-methyl-2-(1,3-benzothiazol-2-yloxy)-acetanilide; S-(2,3,3-trichlorallyl) N,N-diisopropyl-thiolcarbamate; N-(1-ethyl-propyl)-3,4-dimethyl-2,6-dinitroaniline; 3,5-dibromo-4-hydroxy-benzonitrile; and methyl [2-[4-(2,4-dichlorophenoxy)-phenoxy]-propionate, where appropriate, are also of advantage. Surprisingly, some mixtures also exhibit a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

When used as growth regulators, the active compounds according to the invention can likewise be present in the formulations as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, coating and the like. Furthermore, it is possible to apply the active compounds in accordance with the ultra-low volume process or to inject the active compound preparation or the active compound itself into the soil. It is also possible to treat the seeds of plants.

The amounts applied can be varied within a substantial range. In general, 0.01 to 50 kg, preferably 0.05 to 10 kg, of active compound are used per hectare of soil surface.

As regards the time of application, the growth regulators are applied within a preferred period of time, the exact definition of which depends on the climatic and vegetative circumstances.

The preparation and use of the active compounds according to the invention can be seen from the following examples.

Preparation Examples

EXAMPLE 1

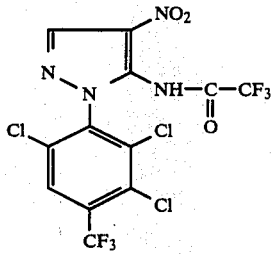

(Process b)

2.4 ml (0.0258 mol) of acetic anhydride and 1.1 ml (0.025 mol) of 98% strength nitric acid are added in succession to 10 g (0.0235 mol) of 5-trifluoroacetamido-1-(2,3,6-trichloro-4-trifluoromethyl-phenyl)-pyrazole in 20 ml of glacial acetic acid at room temperature. After the mixture has been stirred for 20 hours, it is concentrated in vacuo, the residue is taken up in 100 ml of methylene chloride and the mixture is extracted with 400 ml of 5% strength aqueous sodium carbonate solution. The aqueous phase is acidified and extracted with 200 ml of methylene chloride. The combined organic phases are dried over sodium sulphate and freed from the solvent in vacuo. 8.6 g (77.6% of theory) of 4-nitro-5-trifluoroacetamido-1-(2,3,6-trichloro-4-trifluoromethyl-phenyl)-pyrazole of melting point 136°–137° C. are obtained.

EXAMPLE 2

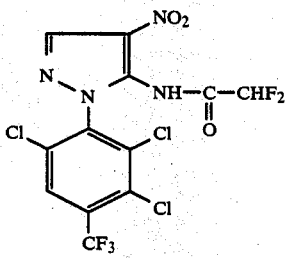

(Process b) 1.4 ml (0.0145 mol) of acetic anhydride and 0.6 ml (0.0139 mol) of 98% strength nitric acid are added in succession to 5.4 g (0.0132 mol) of 5-difluoroacetamido-1-(2,3,6-trichloro-4-trifluoromethyl-phenyl)-pyrazone in 30 ml of glacial acetic acid at room temperature. After the reaction mixture has been stirred for 20 hours, it is poured into 500 ml of water and the crystalline precipitate is filtered off with suction and dried. 5.4 g (91% of theory) of 5-difluoroacetamido-4-nitro-1-(2,3,6-trichloro-4-trifluoromethyl-phenyl)-pyrazole of melting point 146°–151° C. are obtained.

The following 5-fluoroacylamino-4-nitro-1-aryl-pyrazoles of the general formula (I) are obtained in a corresponding manner and in accordance with the general statements on the preparation:

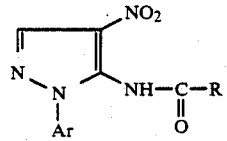

TABLE 2

| Example No. | R | Ar | Melting point (°C.) |
|---|---|---|---|
| 3 | —CF$_3$ | 2,6-Cl, 4-CF$_3$ phenyl | 145 |
| 4 | —CF$_3$ | 2-Cl, 4-CF$_3$ phenyl | 98–101 |
| 5 | —CF$_3$ | 2,6-Cl, 4-SO$_2$CF$_3$ phenyl | 166–168 |
| 6 | —CCl$_2$F | 2,6-Cl, 4-CF$_3$ phenyl | 128–137 |
| 7 | —CHF$_2$ | 2,6-Cl, 4-CF$_3$ phenyl | 93–108 |
| 8 | —CF$_3$ | 2-Cl, 4-OCF$_3$ phenyl | 59–80 |
| 9 | —CClF$_2$ | 2,6-Cl, 4-CF$_3$ phenyl | 116–119 |
| 10 | —CClF$_2$ | 2,3,6-Cl, 4-CF$_3$ phenyl | 105–115 |

TABLE 2-continued

| Example No. | R | Ar | Melting point (°C.) |
|---|---|---|---|
| 11 | —CClF₂ | 2,6-Cl₂-4-SO₂CF₃-phenyl | 171–173 |
| 12 | —CF₃ | 2,6-Cl₂-4-SO₂—CClF₂-phenyl | 168–170 |
| 13 | —CF₃ | 2-Cl-6-Br-4-CF₃-phenyl | 138–143 |
| 14 | —CF₃ | 2-Br-4-CF₃-phenyl | — |
| 15 | —CF₃ | 2-Cl-6-F-4-CF₃-phenyl (3-Cl) | 139–145 |

Preparation of the starting compounds

EXAMPLE IV-1:

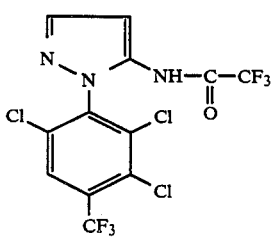

3.1 Ml (0.039 mol) of anhydrous pyridine and 5.5 ml (0.038 mol) of trifluoroacetic anhydride are added in succession to 12 g (0.0363 mol) of 5-amino-1-(2,3,6-trichloro-4-trifluoromethyl-phenyl)-pyrazole in 65 ml of methylene chloride at 0° C. to 5° C., while stirring, and the mixture is stirred at room temperature for 6 hours. For working up, 50 ml of methylene chloride are added, the mixture is washed in succession with dilute hydrochloric acid and aqueous sodium bicarbonate and sodium chloride solution, the organic phase is dried over magnesium sulphate and the solvent is removed in vacuo. 14.6 g (94.3% of theory) of 5-trifluoroacetamido-1-(2,3,6-trichloro-4-trifluoromethyl-phenyl)-pyrazole of melting point 140°–145° C. are obtained.

The following 5-fluoroacylamino-1-aryl-pyrazoles which are unsubstituted in the 4-position, of the general formula (IV), are obtained in a corresponding manner and in accordance with the general statements on the preparation:

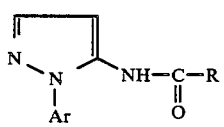
(IV)

TABLE 3

| Example No. | R | Ar | Melting point (°C.) |
|---|---|---|---|
| IV-2 | —CHF₂ | 2,6-Cl₂-3-Cl-4-CF₃-phenyl | 120–125 |
| IV-3 | —CF₃ | 2,6-Cl₂-phenyl | 152–157 |
| IV-4 | —CF₃ | 2-Cl-4-CF₃-phenyl | 150–153 |
| IV-5 | —CF₃ | 2,6-Cl₂-4-SO₂CF₃-phenyl | 162–164 |
| IV-6 | —CCl₂F | 2,6-Cl₂-3-Cl-4-CF₃-phenyl | 151–164 |
| IV-7 | —CHF₂ | 2,6-Cl₂-4-CF₃-phenyl | 121–132 |
| IV-8 | —CF₃ | 2-Cl-4-OCF₃-phenyl | 112–115 |

TABLE 3-continued

| Example No. | R | Ar | Melting point (°C.) |
|---|---|---|---|
| IV-9 | —CClF$_2$ | 2,4-dichloro-5-CF$_3$-phenyl | 155–158 |
| IV-10 | —CClF$_2$ | 2,3,5-trichloro-4-CF$_3$-phenyl | 160–169 |
| IV-11 | —CClF$_2$ | 2,5-dichloro-4-SO$_2$CF$_3$-phenyl | 139–144 |
| IV-12 | —CF$_3$ | 2,5-dichloro-4-SO$_2$CClF$_2$-phenyl | 151–154 |
| IV-13 | —CF$_3$ | 2-Br-4-CF$_3$-5-Cl-phenyl | 170 |
| IV-14 | —CF$_3$ | 2-Br-4-CF$_3$-phenyl | — |
| IV-15 | —CF$_3$ | 2-Cl-3-F-4-CF$_3$-5-Cl-phenyl | 148–151 |

USE EXAMPLES

The compound shown below was employed as the comparison substance in the use examples which follow:

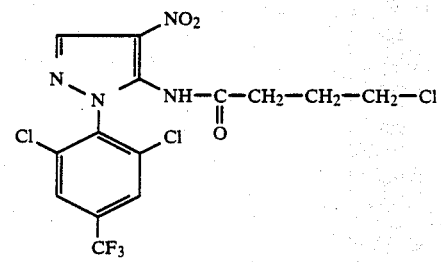

(A)

5-(ω-Chlorobutyramido)-4-nitro-1-(2,6-dichloro-4-trifluoromethyl-phenyl)-pyrazole (known from U.S. Pat. No. 4,614,533)

EXAMPLE A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, a clearly superior activity to comparison substance (A) is shown, for example, by the compound according to the preparation Example 1.

EXAMPLE B

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compounds desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, a clearly superior activity to comparison substance (A), coupled with a comparable selectivity towards useful plants, is shown, for example, by the compound according to preparation Example 1.

EXAMPLE C

Defoliation and desiccation of the leaves of cotton
Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Cotton plants are grown in a greenhouse until the 5th secondary leaf has unfolded completely. In this stage, the plants are sprayed with the preparation of active compound until dripping wet. After 1 week, the shedding of leaves and the desiccation of the leaves are rated, in comparison with the control plants.

In this test, for example, the compounds according to preparation examples 1, 3, 4, 5, 6 and 7 are clearly superior in comparison with the untreated control.

It will be appreciated that the instant specification and examples are set forth by way of illustration and not limitation, and that various modifications and changes may be made without departing from the spirit and scope of the present invention.

We claim:
1. A 5-fluoroacylamino-4-nitro-1-aryl pyrazole of the formula

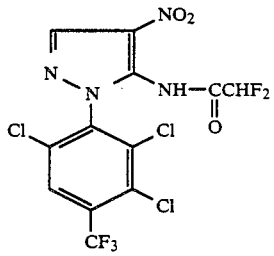

2. A method of killing plants which comprises applying to said plants or to a locus in which said plants are growing or are to be grown, a herbicidally effective amount of the 5-fluoroacylamino-4-nitro-1-aryl pyrazole according to claim 1.

3. A method of regulating the growth of plants which comprises applying to said plants or to a locus in which said plants are growing or are to be grown, a plant-growth regulating effective amount of the 5-fluoroacylamino-4-nitro-1-aryl pyrazole according to claim 1.

* * * * *

UNITED STATES PATENT AND TRADEMARK OFFICE
CERTIFICATE OF CORRECTION

PATENT NO. : 4,808,209

DATED : February 28, 1989

INVENTOR(S) : Reinhold Gehring, et al

It is certified that error appears in the above-identified patent and that said Letters Patent is hereby corrected as shown below:

| | |
|---|---|
| Col. 12, line 53 | After "benzine" insert --benzene-- |
| Col. 15, line 67 | Delete "aminno" and substitute --amino-- |
| Col. 19, line 55 | Delete "Ml" and substitute --ml-- |
| Col. 22, line 56 | Delete "compounds" and substitute --compound-- |
| Col. 23, line 15 | Delete "preparation" and substitute --preparations-- |

Signed and Sealed this

Twenty-first Day of November, 1989

Attest:

JEFFREY M. SAMUELS

*Attesting Officer*    *Acting Commissioner of Patents and Trademarks*